United States Patent [19]

Ikeda et al.

[11] 4,209,628

[45] Jun. 24, 1980

[54] PROCESS FOR PREPARING 2-OXAZOLIDONE AND ITS DERIVATIVES

[75] Inventors: Sakuji Ikeda, Tokyo; Kazuo Soga, Yokohama, both of Japan

[73] Assignee: Tokyo Institute of Technology, Tokyo, Japan

[21] Appl. No.: 900,160

[22] Filed: Apr. 26, 1978

Related U.S. Application Data

[63] Continuation of Ser. No. 779,335, Mar. 21, 1977, abandoned.

[30] Foreign Application Priority Data

Apr. 20, 1976 [JP] Japan ................................. 51-45787

[51] Int. Cl.$^2$ ........................................... C07D 263/22
[52] U.S. Cl. ..................................... 548/229; 548/231
[58] Field of Search .................... 260/307 C; 548/229, 548/231

[56] References Cited

U.S. PATENT DOCUMENTS

| 2,868,801 | 1/1959 | Steele | 260/307 C |
| 3,247,220 | 4/1966 | Ham | 260/307 C |

*Primary Examiner*—Jose Tovar
*Attorney, Agent, or Firm*—Burgess, Ryan and Wayne

[57] ABSTRACT

Process for preparing 2-oxazolidone and its derivatives by reacting react carbon dioxide with aziridine compound, preferably, in the presence of Lewis acid as a catalyst.

7 Claims, No Drawings

PROCESS FOR PREPARING 2-OXAZOLIDONE AND ITS DERIVATIVES

This is a continuation of application Ser. No. 779,335, filed Mar. 21, 1977, now abandoned.

BACKGROUND OF THE INVENTION 2-oxazoidone and its derivatives are represented by the following formula:

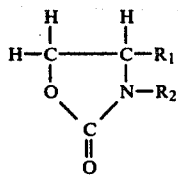

2-oxazolidone has the following formula:

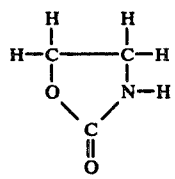

A derivative of 2-oxazolidone such as 4-methyl-2-oxazolidone has the following formula:

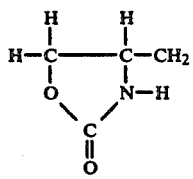

Such 2-oxazolidone and its derivatives are useful as intermediates in the preparation of drugs, and polymers of 2-oxazolidone derivatives are used, for example, in preparation of fibers, tablet coatings, lubricant additives, cigarette filters, rust inhibitors and dyeing assistants.

Many conventional processes for preparing 2-oxazolidone and its derivatives are known. 2-oxazolidone may be prepared by the reaction as shown below:

the reaction of β-aminoalcohol with a compound selected from the group consisting of phosgene, dialkylcarbonate, carbon dioxide, urea, isocyanate, ethylchlorocarbonate, carbon disulfide;

the reaction of epoxide with a compound selected from the group consisting of cyanuric acid, urea and cyanamide;

the reaction of acrolein with isocyanate; or the removal of hydrochloric acid from β-hydroxyalkylsemicarbazide.

However, such conventional processes have disadvantages, for example, high cost of starting raw materials, complexity of the procedure or low yield of 2-oxazolidone and its derivatives.

It is an object of the present invention to provide a process of preparing 2-oxazolidone and its derivatives at a low cost and a high yield.

SUMMARY OF THE INVENTION

The present invention relates to a process for preparing 2-oxazolidone and its derivatives.

2-oxazolidone and its derivatives have the following general formula:

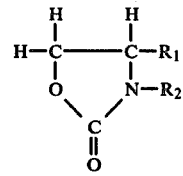

wherein $R_1$ is hydrogen, a lower alkyl group of 1 to 4 carbon atoms, phenyl and benzyl, and $R_2$ is hydrogen, a lower alkyl group of 1 to 4 carbon atoms, a substituted lower alkyl group such as β-cyanoethyl, β-aminopropyl, α-hydroxyethyl and β-chloroethyl, unsubstituted or substituted phenyl, benzyl, an acyl group such as formyl, acetyl, propionyl, benzoyl, toluoyl, acryloyl and methacryloyl.

The process of the present invention comprises reacting carbon dioxide with an aziridine compound.

Aziridine compounds include aziridine and its derivatives represented by the following formula:

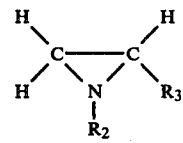

wherein $R_1$ and $R_2$ are as hereinbefore defined.

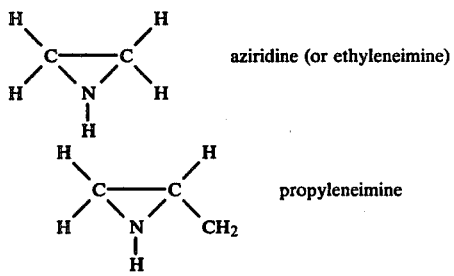

The reaction of carbon dioxide with an aziridine compound may be carried out in a solvent. Such solvents include saturated paraffinic hydrocarbons such as n-heptane, aromatic hydrocarbons such as benzane, substituted aromatic hydrocarbons such as o-dichlorobenzene, cycloparaffins such as cyclohexane, alcohols such as methanol and ethanol, ethers such as diethylether, ketones such as acetone, halogenated hydrocarbons such as chloroform, cyclic esters such as tetrahydrofuran, sulfoxides such as dimethyl sulfoxide, and amides such as formamide.

The reaction of the present invention may be carried out at a temperature of 0° C. to 200° C., preferably 20° C. to 120° C., by using a mixture of carbon dioxide and aziridine compound in the molar ratio ($CO_2$/aziridines) of 0.1 to 1,000, preferably 1 to 100.

The reaction of the present invention may effectively be carried out in the presence of Lewis acid as a catalyst.

Preferred Lewis acids used as a catalyst in the present invention include halogens such as chlorine, bromine and iodine, halogenides of titanium, aluminium, manganese, copper, tin, antimony, iron, zinc, phosphorus and boron.

DESCRIPTION OF THE PREFERRED EMBODIMENTS

The following examples are given by way of illustration only:

EXAMPLE 1

2.5 l (S.T.P.) of carbon dioxide, 3.2 g of propyleneimine, 75 mg of iodine and 8.0 g of chloroform were placed in a stainless steel high-pressure tube of about 300 ml in volume. After the mixture was allowed to react at a temperature of 30° C. for 31 hours, the reaction product was taken out of the high-pressure tube and distilled under reduced pressure to obtain 2.4 g of pure 4-methyl-2-oxazolidone, which has the properties as shown below:

b.p. 128°–130° C. (3 mmHg); n.m.r. (CDCl$_3$) δ 1.3(3H, CH$_3$, d), 4.0(1H, CH$_2$ and 1H, CH, m), 4.5(1H, CH$_2$, S) and 6.7(1H, NH, broad); i.r. ν$_{max}$ 1735 and 1240cm$^{-1}$;

| Analysis: | C(%) | H(%) | N(%) |
|---|---|---|---|
| Found | 47.38 | 7.10 | 14.35 |
| Calculated for C H$_2$NO$_3$ | 42.81 | 6.53 | 13.86 |

EXAMPLE 2

3 l (S.T.P.) of carbon dioxide, 3.2 g of ethyleneimine, 50 mg of zinc chloride and 20 g of ethanol were placed in a stainless steel high-pressure tube of 300 ml in volume. After the mixture was allowed to react at a temperature of 60° C. for 50 hours, the reaction product was taken out of the high-pressure tube and recrystallized from chloroform solution of the reaction product to obtain 1.5 g of pure 2-oxazolidone, which has the properties as shown below:

m.p. 86°–88° C.; n.m.r. (D$_2$O) δ 4.14(2H, CH$_2$, t), 5.02(2H, CH$_2$, t); i.r. ν$_{max}$ 1735, 1256, 1085, 1023, 970 and 920cm$^{-1}$;

| Analysis: | C(%) | H(%) | N(%) |
|---|---|---|---|
| Found | 41.70 | 5.87 | 16.11 |
| Calculated for C$_2$H$_4$NO$_2$ | 41.38 | 8.75 | 16.09 |

EXAMPLE 3-7

The same procedure as that described in Example 1 was repeated except that the procedure was carried out under the conditions as shown below to obtain pure 4-methyl-2-oxazolidone:

| Example No. | Carbon dioxide (l) (S.T.P.) | Propyleneimine (g) | Catalyst (Lewis acid) (mg) | Solvent (g) | Reaction temperature (°C.) | Reaction time (hour) | 4-methyl-2-oxazolidone (g) |
|---|---|---|---|---|---|---|---|
| 3 | 2.4 | 3.5 | ferric chloride 50 | hexane 20 | 100 | 50 | 1.2 |
| 4 | 7 | 4 | phosphorus trichloride 50 | acetone 50 | 20 | 48 | 3.5 |
| 5 | 5 | 3.2 | antimony tribromide 60 | benzene 60 | 75 | 52 | 3 |
| 6 | 3 | 3.5 | tin tetrachloride 50 | — | 50 | 48 | 1.5 |
| 7 | 5 | 4 | — | chloroform 30 | 80 | 50 | 0.3 |

EXAMPLE 8-10

The same procedure as that described in Example 2 was repeated except that the procedure was carried out under the conditions as shown below to obtain pure 2-oxazolidone:

| Sample No. | Carbon dioxide (l) (S.T.P.) | Ethyleneimine (g) | Catalyst (Lewis acid) (mg) | Solvent (g) | Reaction temperature (°C.) | Reaction time (hour) | 2-oxazolidone (g) |
|---|---|---|---|---|---|---|---|
| 8 | 10 | 3 | iodine 30 | methylene chloride 80 | 80 | 20 | 1.8 |
| 9 | 5.5 | 3.2 | copper iodide 80 | tetrahydrofuran 30 | 80 | 73 | 0.9 |
| 10 | 10 | 3 | — | methylene chloride 80 | 80 | 50 | 0.2 |

EXAMPLE 11-16

The same procedure as that described in Example 1 was repeated except that the procedure was carried out in a stainless steel high-pressure tube of about 50 ml under the conditions as shown below to obtain 2-oxazolidone derivatives such as N-(β-cyanoethyl)-2-oxazolidone, 3-acryloyl-2-oxazolidone and 3-phenyl-2-oxazolidone:

| Example No. | Carbon dioxide (l) (S.T.P.) | Aziridine compound (g) | Catalyst (Lewis acid) (mg) | Solvent (g) | Reaction temperature (°C.) | Reaction time (hour) | 2-oxazolidone derivative (g) |
|---|---|---|---|---|---|---|---|
| 11 | 3 | N-(β-cyano-ethyl)-ethylene-imine 1 | ferric chloride 30 | n-heptane 8 | 70 | 24 | 3-(β-cyano-ethyl)-2-oxazolidone 1.1 |
| 12 | 3 | N-(β-cyano-ethyl)-ethylene-imine 1 | antimony trichloride 30 | chloroform 10 | 70 | 30 | 3-(βcyano-ethyl)-2-oxazolidone 1.3 |
| 13 | 3 | N-(β-cyano-ethyl)-ethylene-imine 1 | alumium chloride 30 | o-dichloro-benzene 5 | 80 | 30 | 3-(β-cyano-ethyl)-2-oxazolidone 0.3 |
| 14 | 3 | N-β-cyano-ethyl)-ethylene-imine 1 | — | chloroform 5 | 80 | 24 | 3-(βcyano-ethyl)-2-oxazollicone 0.2 |
| 15 | 3 | N-acryloyl-ethylene-imine 3 | iodine 60 | dioxane 10 | 60 | 30 | 3-acryloyl-2-oxazolidone 2.1 |
| 16 | 2 | N-phenyl-ethylene-imine 3 | bromine 60 | tetrahydro-furan 10 | 60 | 24 | 3-phenyl-2-oxazolidone 1.2 |

We claim:
1. A process for preparing 2-oxazolidone compounds of the formula

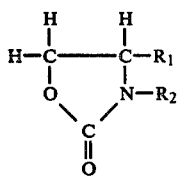

which comprises reacting carbon dioxide with an aziridine compound of the formula

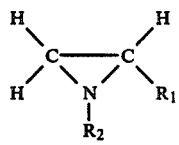

at a temperature of from 0° to 200° C., and a mol ratio of carbon dioxide to said aziridine compound of from 0.1 to 1000, wherein $R_1$ is selected from the group consisting of hydrogen, lower alkyl of 1 to 4 carbon atoms, phenyl and benzyl and $R_2$ is selected from the group consisting of hydrogen, lower alkyl of 1 to 4 carbon atoms, β-cyanoethyl, β-aminopropyl, α-hydroxyethyl, β-chloroethyl, phenyl, benzyl, and acyl selected from the group consisting of formyl, acetyl, propionyl, benzoyl, toluoyl, acryloyl and methacryloyl.

2. A process for preparing 2-oxazolidone compounds according to claim 1, comprising reacting carbon dioxide with said aziridine compound in the presence of a Lewis acid catalyst.

3. A process according to claim 2 wherein said Lewis acid is selected from the group consisting of halogens and halogenides of titanium, aluminium, manganese, copper, tin, antimony, iron, zinc, phosphorus and boron.

4. A process according to claim 3, wherein said halogens are chlorine, bromine and iodine and said halogenides are chlorides, bromides and iodides.

5. A process according to claim 1, wherein said reaction is conducted in a solvent selected from the group consisting of saturated paraffinic hydrocarbons, aromatic hydrocarbons, cycloparaffinic hydrocarbons, alcohols, ethers, ketones, halogenated hydrocarbons, cyclic ethers, and amides.

6. A process according to claim 1, wherein said molar ratio is 1 to 100.

7. A process according to claim 1, wherein said temperature is 20°–120° C.

* * * * *

UNITED STATES PATENT OFFICE
CERTIFICATE OF CORRECTION

Patent No. 4,209,628  Dated June 24, 1980

Inventor(s) Sakuji Ikeda, et al

It is certified that error appears in the above-identified patent and that said Letters Patent are hereby corrected as shown below:

Column 1, third formula down:  "$CH_2$" should be --$CH_3$--.

Column 2, second formula down:  "$R_3$" should be --$R_1$--.

fourth formula down:  "$CH_2$" should be --$CH_3$--.

line 53:  "benzane" should be --benzene--.

Column 3, line 62:  "6.53" should be --6.93--.

Column 4, line 14:  "8.75" should be --5.75--.

line 14:  "$C_2H_4NO_2$" should be --$C_2H_5NO_2$--.

Columns 3-4, in the chart for "EXAMPLES 3-7", in "Example No. 5":
    "antimony tribromide 60" should be
    --antimony tribromide 50--.

Columns 3-4, in the chart for "EXAMPLES 8-10", in "Sample No. 9":
    "copper iodide 80" should be --copper iodide 50--.

Signed and Sealed this

Twenty-fourth Day of February 198.

[SEAL]

Attest:

RENE D. TEGTMEYER

Attesting Officer      Acting Commissioner of Patents and Trademar